United States Patent [19]

Sick

[11] 4,116,566

[45] Sep. 26, 1978

[54] LINE SCANNING DEVICE FOR DETECTING DEFECTS IN WEBS OF MATERIAL

[75] Inventor: Erwin Sick, Icking, Fed. Rep. of Germany

[73] Assignee: Erwin Sick Gesellschaft mit beschränkter Haftung Optik-Elektronik, Waldkirch, Fed. Rep. of Germany

[21] Appl. No.: 738,546

[22] Filed: Nov. 3, 1976

[30] Foreign Application Priority Data

Nov. 12, 1975 [DE] Fed. Rep. of Germany ....... 2550814

[51] Int. Cl.² ............................................ G01N 21/16
[52] U.S. Cl. ...................................... 356/200; 350/6; 350/7; 350/96.10
[58] Field of Search ................... 350/6, 7, 55, 175 TS, 350/299, 294, 6.1–6.7, 7.55; 356/199, 200; 358/84, 199; 250/234–236; 355/38, 34, 35, 36–37, 24; 255/234, 563, 572

[56] References Cited

U.S. PATENT DOCUMENTS

| | | | |
|---|---|---|---|
| 3,317,738 | 12/1964 | Piepenbrink et al. | 356/200 |
| 3,758,197 | 9/1973 | Klang et al. | 350/285 |
| 4,004,153 | 1/1977 | Obser et al. | 356/200 |
| 4,007,992 | 2/1977 | Petrohilos et al. | 350/7 |
| 4,052,120 | 10/1977 | Sick et al. | 350/6 |

OTHER PUBLICATIONS

Richards, Photodector as a Function Detector, Aug. 1970, vol. 13, No. 3, IBM Technical Disclosure Bulletin.

Primary Examiner—John K. Corbin
Assistant Examiner—B. W. de los Reyes

[57] ABSTRACT

A line scanning device for detecting defects in webs of material, wherein a laser light source throws a light spot by way of an objective, a light deflector device, and a cylindrical lens onto a web of material moving parallel to its surface, the light spot periodically scanning the web at right angles to the direction of its movement and parallel to its surface, and wherein a light receiving arrangement comprising a rod light guide and at least one photoreceiver is disposed parallel to the web of material and to the direction of scanning. The rod light guide carries a step mirror arrangement on that side of its periphery lying opposite the light inlet, and a light-scattering cylindrical lens grid, the axes of whose lenses extend in the scanning direction, is disposed between the light source and the objective.

22 Claims, 5 Drawing Figures

LINE SCANNING DEVICE FOR DETECTING DEFECTS IN WEBS OF MATERIAL

The invention relates to a line scanning device for detecting defects in webs of material, wherein a laser light source throws a light spot by way of an objective, a light deflector device, and a cylindrical lens onto a web of material moving parallel to its surface, the said light spot periodically scanning the web at right angles to the direction of its movement and parallel to its surface, and wherein a light receiving arrangement comprising a rod light guide and at least one photoreceiver is disposed parallel to the web of material and to the direction of scanning.

Devices of this kind work either with the light reflected back by the web of material or by that passing through it. The light receiving arrangement is preferably disposed at the angle of reflection of the incident light, in order to achieve the highest possible light yield.

Known line scanning devices nevertheless have the disadvantage that any scratches existing in the longitudinal direction, that is to say in the direction of movement of the web, particularly on sheet metal surfaces, can be recognised only with difficulty, while moreover the proportion of light reaching the photoreceiver is very small because losses through scattering and total reflection in the rod light guide are relatively high.

For this reason it has already been proposed (German Patent Application P No. 25 08 366.3) to provide on one peripheral side of the rod light guide a step or grid mirror arrangement which consists of a multiplicity of plane mirrors disposed against one another and tilted by a determined angle relative to the axis of the rod. The angle of the plane mirrors in relation to the optical axis is such that light falling from inside onto the plane mirrors substantially at right angles to the axis of the rod is reflected to the opposite side of the rod at an angle such that the light beam undergoes total reflection inside the rod until it impinges on one of the end faces of the rod, from which it then passes into the photoreceiver or onto a plane mirror reflecting it back into the rod.

With the arrangement proposed it may however, occur that after total reflection on the opposite side of the rod the light which has once been reflected by the step mirror arrangement will impinge again on the latter, which entails losses of light and is also undesirable for reasons of homogeneity.

The present invention therefore seeks to provide a line scanning device of the kind first mentioned above, in which a high light yield is achieved at the photoreceiver and additional disadvantages through light losses or inhomogeneity are avoided.

In order to solve this problem the invention provides for the rod light guide to carry a step mirror arrangement on the side of its periphery opposite the light inlet, and for a light-scattering cylindrical lens grid (i.e., a grid of cylindrical lenses), the axes of whose lenses extend in the scanning direction, to be disposed between the light source and the objective. A cylindrical lens, which concentrates the light on the step mirror arrangement, is expediently disposed between the web of material and the light guide rod.

As the result of this arrangement the sharply focused laser beam is fanned out at right angles to the direction of deflection movement in such a manner that it completely and homogeneously illuminates the objective and the light deflection device, which is preferably in the form of a mirror wheel, at right angles to the direction of deflection. This has the consequence that the light thrown back by the web of material, preferably at the angle of reflection, also fully and homogeneously illuminates the cylindrical lens of the receiving arrangement. The light falling on the rod light guide from the cylindrical lens thus falls on the step mirror arrangement at different angles to the tangent of the rod light guide, so that light totally reflected inside the preferably circular rod light guide does not impinge again on the step mirror arrangement. Thus inhomogeneities resulting from repeated impingement of the light on the step mirror arrangement do not occur and a better light yield is achieved.

In a first advantageous embodiment the cylindrical lens grid is situated at the focal point of the objective. In this arrangement a sharp punctiform light spot appears on the web of material.

It is however preferable for the cylindrical lens grid to be situated slightly in front of or behind the focal point of the objective, the distance from the focal point expediently amounting to from 5 to 20 percent, preferably 10 percent, of the focal length of the objective. In this embodiment a narrow line of light, extending in the direction of the movement of the web of material, appears on the latter. This is advantageous particularly in the detection of scratches which on sheet metal surfaces extend in the direction of movement of the web, because the thin light line then extends in the same direction as the scratches, which would otherwise be very difficult to detect. This particular embodiment is therefore especially suitable for detecting longitudinal scratches on sheet metal surfaces.

It is preferable for the cylindrical lens grid to be displaceable in the direction of the optical axis, so that the optimum length of the light line on the web of material can be adjusted.

Good homogeneity together with a high light yield is achieved if the cross-section of the light beam falling on the cylindrical lens grid covers at least five juxtaposed negative lenses of the cylindrical lens grid.

In order still more effectively to prevent light from impinging a plurality of times on the step mirror arrangement, it is expedient for the rod light guide to be round. The diameter of the rod light guide should be at least five to ten times, preferably twenty times, as great as the width of the step mirror arrangement.

An advantageous embodiment is characterised in that the light beam passes through a beam widening optical system before it impinges on the objective. The widening has the effect of fanning out the laser beam in both directions.

The step mirror arrangement has in addition the disadvantage that during scanning the fundamental frequency corresponding to the distance between the individual plane mirrors appears in the reception signal. This effect can be at least substantially reduced by providing between the web of material and the light receiving arrangement of light-scattering cylindrical lens grid comprising negative cylindrical lenses extending at right angles to the axis of the rod light guide. The arrangement is expediently such that the light beam, which in this way is also fanned out in the direction of the axis of the rod, simultaneously covers a plurality of plane mirrors of the step mirror arrangement.

Since at the end face of the rod light guide a light pattern appears which varies considerably during the scanning and since the surfaces of normal photoreceivers, such as multipliers, have very different sensitivities over their surface, in order to achieve further homogenisation of the output signal provision is made for the light inlet of an Ulbricht sphere, at the light output of which the photoreceiver is disposed, to be provided on at least one end face of the rod light guide. The expression "Ulbricht sphere" is understood to mean an opaque hollow sphere the interior of which is coated with a preferably white light-scattering material and which at points preferably lying 90° apart is provided with a light inlet and a light outlet. The direct light path from the light inlet to the light outlet should be interrupted by a diaphragm, so that all the light appearing at the outlet reaches the latter only after the light has been scattered a number of times on the inner surface of the sphere.

At the other end of the rod light guide there may expediently also be provided an Ulbricht sphere or a mirror coating, the mirror coating ensuring that the light impinging there is reflected back into the rod to the other end face.

The invention is described below by way of example with reference to the accompanying drawings, in which:

FIG. 1d is a view in the direction of the arrow D in FIG. 1a; and

Figure 1A:
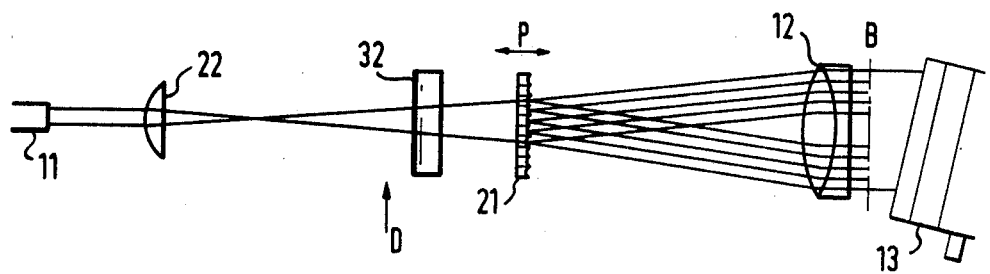
FIGS. 1a, 1b and 1c are diagrammatical views of a preferred embodiment of the line scanning device of the invention, the three Figures having to be imagined to be placed against one another at the points A and B.
Figure 1D:
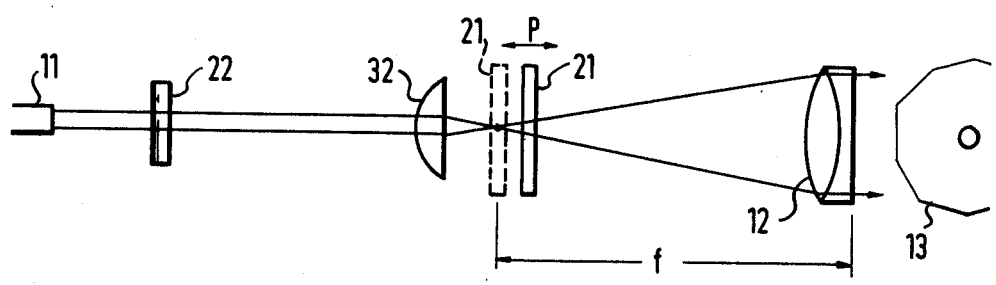

According to FIGS. 1a and 1d the light beam of a laser 11 passes through a cylindrical lens 22, which has a focal length of 50 mm for example, and through another cylindrical lens 32, which is disposed in a crossed relationship thereto and which has a focal length of 5 mm for example, into the cylindrical lens grid 21 which is provided in accordance with the invention and which is disposed at a distance from the objective 12 which is slightly shorter than the focal length $f$ of the latter. The grid may be displaceable in the directions of the double arrow P, so that it may also lie at the focal point or at a defined distance therefrom.

Figure 1B:
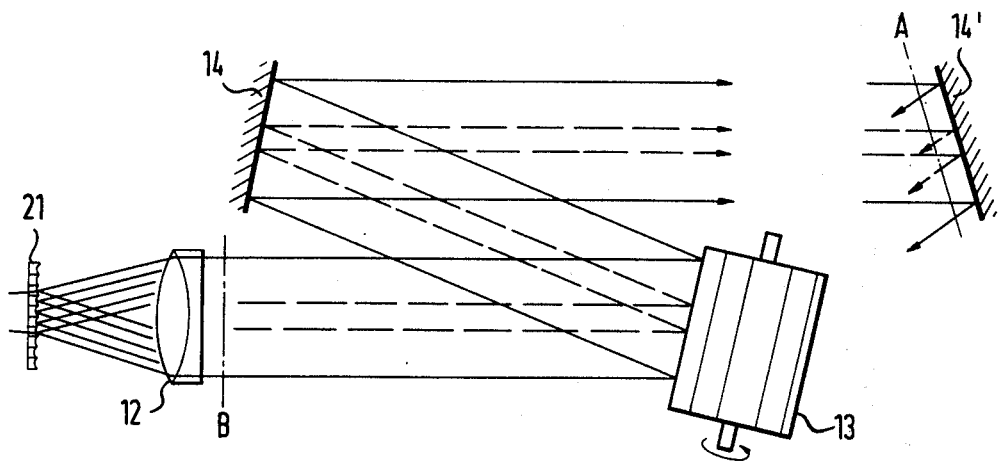

According to FIG. 1b there is disposed behind the objective 12 a mirror wheel 13 which constitutes the light deflecting device and which is also indicated in FIGS. 1a and 1b in order to define the position of its axis in relation to the axes of the cylindrical lenses 22, 32 which is essential to the invention. The axis of the mirror wheel 13 is slightly tilted so that the reflected light can fall on an elongated plane mirror 14 which is disposed at the side of the light emitting arrangement and extends at right angles to the plane of the drawing over the entire width of the apparatus (corresponding to the width of the web of material or the scanning range of the mirror wheel). In order to reduce the size of the drawings, the tilting of the mirror wheel 13 is greatly exaggerated in FIG. 1b.

The light reflected by the plane strip mirror 14 passes on to another plane strip mirror 14' at the other end of the apparatus, and thence through reflection passes obliquely downwards (deflection obliquely upwards would be equally possible) to a spherical or cylindrical mirror 14" whose axis lies in the plane of the drawing and whose focal point or focal line is situated on the illuminated surface of the mirror wheel 13. The objective 12 and the cylindrical mirror 14" concentrate the light together with a cylindrical lens 15 which is disposed directly in front of the web of material M (FIG. 1c) and whose axis is at right angles to the plane of the drawing, while its focal line is situated on the surface of the web of material M at a position 16. An exact light spot would be formed if the cylindrical lens grid 21 were disposed at a distance from the objective 12 which is exactly equal to the focal length $f$ (shown in dashed lines in FIG. 1d), which is entirely possible. Through a defined displacement of the focal point in accordance with FIG. 1d, a line of light is formed in the direction of the arrow P on the web of material, which is indicated by the optical path shown in dash-dotted lines. The light spot 16 or line of light moves to-and-fro on the web of material M at right angles to the plane of the drawing in FIG. 1c on the rotation of the mirror wheel 13. The web of material M in turn moves in the direction of the arrow P, that is to say at right angles to the direction of scanning, which in FIG. 2 is indicated by a double arrow s.

A light receiving arrangement 17 is provided near the web of material, preferably at an angle to the incoming light beam which is equal to the angle of reflection, this arrangement consisting of another cylindrical lens 28, which extends parallel to the cylindrical lens 15, and of a rod light guide 18 whose axis likewise extends parallel to the axes of the cylindrical lenses 15 and 28. The focal length of the cylindrical lens 28 is so selected, taking into account the refractive power of the rod light guide 18, that the light beam according to FIG. 1b is concentrated on a step mirror arrangement 20 which is disposed on the peripheral side diametrically opposite the light inlet side and the construction of which can be seen in detail in FIG. 2.

Figure 2:
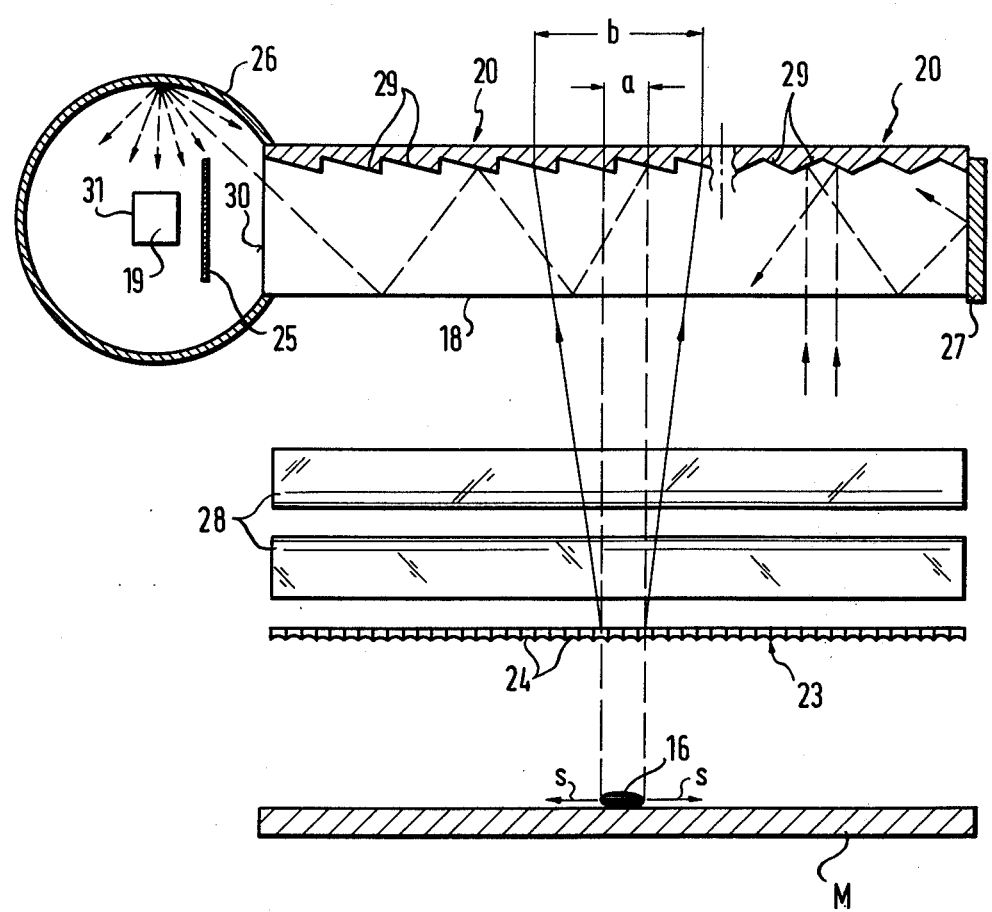
FIG. 2 is a diagrammatical, partly sectional view on the line II—II in FIG. 1c.

The step mirror arrangement consists of individual plane mirrors 29 which are either combined to form a sawtooth arrangement as shown in the left-hand half of FIG. 2 or to form a roof-shaped arrangement as shown in the right-hand half of FIG. 2. In either case the angles of the plane mirrors 29 relative to the axis of the rod light guide 18 should be so selected that light reflected on them impinges on the opposite wall of the rod light guide 18 at the angle of total reflection, so that the beam paths shown in dashed lines in FIG. 2 are obtained.

At the right-hand end of the rod light guide (referring to FIG. 2) a mirror coating 27 is provided, while at the left-hand end face an Ulbricht sphere 26 is provided, on whose inner wall the incoming light is scattered in the manner indicated in dashed lines. The photosensitive surface of a photoreceiver 19 is disposed, at right angles to the light inlet side 30, in an opening 31, which for example is square. Between the light inlet 30 and the light outlet 31 is provided a diaphragm 25 which prevents direct passage of light from the inlet to the outlet.

Figure 1C:
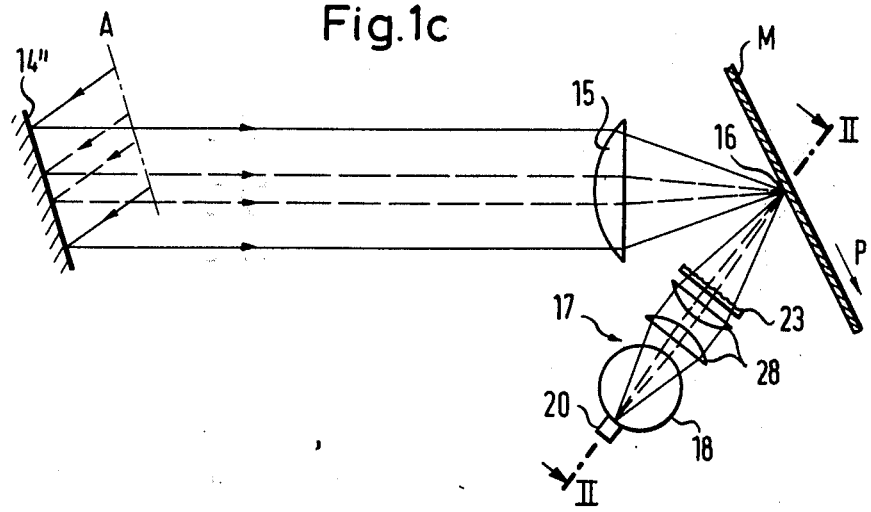

As shown in FIGS. 1c and 2, another cylindrical lens grid 23, whose individual negative cylindrical lenses 24 have their axes at right angles to the axis of the rod light guide 18, is disposed between the web of material M and the cylindrical lens 28.

The mode of operation of the line scanning device of the invention is as follows.

Without the cylindrical lens grid 21 shown in FIGS. 1a and 1b the beam of the laser 11 would not uniformly illuminate the objective 12 and the straight reflecting surface of the mirror wheel 13 in the direction of the mirror wheel axis. The bundle of rays would for example follow the path shown in dashed lines in FIGS. 1a and 1b. Particularly with substantially specular reflection on the web of material M, a very narrow light beam would fall on the step mirror arrangement 20, so that the light totally reflected within the rod would fall twice or more times on the mirror arrangement 20, which is undesirable.

As the result of the arrangement of the cylindrical lens grid 21 according to the invention, however, the fanned-out beam shown in solid lines in FIG. 1 is obtained. As can be seen particularly in FIG. 1c, as the result of this arrangement the light falls on the step mirror arrangement 20 at very different angles relative to the tangent to the rod 18 at the position of the step mirror arrangement 20, so that reflected and totally reflected light substantially no longer passes back to the step mirror arrangement 20 and thus through multiple total reflection passes to the end of the rod, where the measurement (or reflection) takes place.

The action of the additional cylindrical lens grid 23 can be seen particularly clearly in FIG. 2. Whereas without this additional cylindrical lens grid 23 the light beam shown in dashed lines and extending upwards from the light spot 16 would substantially have the width $a$, the cylindrical lens grid 23 fans out the light beam in such a manner that it impinges on the step mirror arrangement 20 with for example the width $b$. The width $b$ is so selected that in all cases two or preferably even more plane mirrors 29 are simultaneously covered by the beam. In this manner the influence of the fundamental frequency of the mirror grid during scanning is substantially eliminated.

The irregularities at the end faces of the rod light guide 18, which are caused by the irregular reflections within the rod light guide 18, are eliminated by the provision of the Ulbricht sphere 26 by which the light passing out of the end face of the rod light guide 18 is scattered in all directions at every impingement point, so that by the time it reaches the photoreceiver 19 extensive homogenisation has been achieved.

Consequently the invention not only provides a very high light yield, but at the same time also avoids the disadvantageous influences of inhomogeneity. It may be pointed out that it is particularly advantageous that through slight displacement of the cylindrical lens grid 21 in the direction of the objective 12, away from the focal point, there is obtained on the web of material M in the direction of movement P a line of light which is suitable for sensitive reproduction of longitudinal scratches in the electric signal obtained at the output of the photoreceiver 19.

A simplified embodiment can also work without the lens grid while retaining adequate sensitivity, in which case however the crossed cylindrical lenses 22, 32 are of particular importance.

What is claimed is:

1. In a line scanning device for detecting defects in webs of material, wherein a laser light source throws a light spot by way of an objective, a light deflector device, and a cylindrical lens onto a web of material moving parallel to its surface, said light spot periodically scanning the web at right angles to the direction of its movement and parallel to its surface, and wherein a light receiving arrangement comprising a rod light guide having a first surface, a second surface opposite said first surface and having a longitudinal axis and at least one photoreceiver is disposed parallel to the web of material and to the direction of scanning; the improvement comprising a step mirror arrangement carried by said rod light guide along said first surface and parallel to said axis, on that side of its periphery lying opposite the light inlet to said guide, and comprising a plurality of mirrors inclined with respect to said longitudinal axis, and arranged substantially exactly one behind the other when looking in the direction of said axis such that light reflected by said mirrors impinges on said second surface at angles of total reflection, and a light-scattering cylindrical lens grid, the axes of whose lenses extend in the scanning direction, disposed between the light source and said objective.

2. A device according to claim 1, wherein the cylindrical lens grid is situated at the focal point of the objective.

3. A device according to claim 1, wherein the cylindrical lens grid is axially displaced slightly from the focal point of the objective.

4. A device according to claim 3, wherein the distance from the focal point amounts to from 5 to 20 percent, of the focal length of the objective.

5. A device according to claim 1, wherein the cylindrical lens grid is displaceable in the direction of the optical axis.

6. A device according to claim 1, wherein the cross-section of the light beam falling on the cylindrical lens grid covers at least five juxtaposed negative lenses of the cylindrical lens grid.

7. A device according to claim 1, wherein the rod light guide is circular.

8. A device according to claim 1, wherein the diameter of the rod light guide is at least five times as great as the width of the step mirror arrangement.

9. A device according to claim 8, wherein said diameter is about twenty times said width.

10. A device according to claim 1, wherein the light beam passes through a beam widening optical system before it impinges on the objective.

11. A device according to claim 10, wherein the widening optical system comprises first and second crossed cylindrical lenses.

12. A device according to claim 11, wherein the axis of the first cylindrical lens extends at right angles to the axis of the mirror wheel.

13. A device according to claim 11, wherein the focal length of the first and second cylindrical lenses are in the ratio of approximately 10:1.

14. A device according to claim 11, wherein the focal line of the second cylindrical lens coincides with the focal point of the objective.

15. A device according to claim 1, wherein a light-scattering cylindrical lens grid comprising negative cylindrical lenses extending at right angles to the axis of the rod light guide is provided between the web of material and the light receiving arrangement.

16. A device according to claim 11, wherein the first cylindrical lens is adapted to be displaceable in the axial direction or exchangeable.

17. A device according to claim 1, wherein between the web of material and the rod light guide a cylindrical lens is disposed which concentrates the light on the step mirror arrangement.

18. A device according to claim 1, wherein the light inlet of an Ulbricht sphere, at whose light outlet the photoreceiver is disposed, is provided at at least one end face of the rod light guide.

19. A device according to claim 18 wherein the direct light path from the light inlet to the light outlet of the Ulbricht sphere is interrupted by a diaphragm.

20. A device according to claim 18, wherein at the other end of the rod light guide an Ulbricht sphere is likewise provided.

21. A device according to claim 18, wherein the light inlet and light outlet openings of the Ulbricht sphere are at right angles to one another.

22. A device according to claim 16, wherein at the other end of the rod light guide a mirror coating is provided.

* * * * *